United States Patent [19]
Yum et al.

[11] Patent Number: 6,001,390
[45] Date of Patent: *Dec. 14, 1999

[54] FORMULATIONS FOR TRANSDERMAL DELIVERY OF PERGOLIDE

[75] Inventors: Su I Yum, Los Altos; Melinda K. Nelson, Sunnyvale; Patricia S. Campbell, Palo Alto, all of Calif.

[73] Assignee: Alza Corporation, Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/768,600

[22] Filed: Dec. 18, 1996

Related U.S. Application Data

[63] Continuation-in-part of application No. 08/473,631, Jun. 7, 1995.

[51] Int. Cl.⁶ .................................................. A61F 13/02
[52] U.S. Cl. .......................................... 424/448; 424/449
[58] Field of Search ...................................... 424/448, 449

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |
| 4,031,894 | 6/1977 | Urquhart et al. | 128/268 |
| 4,144,317 | 3/1979 | Higuchi et al. | 424/21 |
| 4,166,182 | 8/1979 | Kornfeld et al. | 546/67 |
| 4,201,211 | 5/1980 | Chandrasekaran et al. | 128/268 |
| 4,286,592 | 9/1981 | Chandrasekaran | 128/260 |
| 4,314,557 | 2/1982 | Chandrasekaran | 128/260 |
| 4,379,454 | 4/1983 | Campbell et al. | 604/897 |
| 4,435,180 | 3/1984 | Leeper | 604/896 |
| 4,559,222 | 12/1985 | Enscore et al. | 424/28 |
| 4,568,343 | 2/1986 | Leeper et al. | 604/896 |
| 4,573,995 | 3/1986 | Cheng et al. | 604/896 |
| 4,588,580 | 1/1989 | Gale et al. | 424/21 |
| 4,645,502 | 2/1987 | Gale et al. | 604/896 |
| 4,704,282 | 11/1987 | Campbell et al. | 424/449 |
| 4,746,515 | 5/1988 | Cheng | 424/449 |
| 4,788,062 | 11/1988 | Gale et al. | 424/449 |
| 4,797,405 | 1/1989 | Conine et al. | 514/288 |
| 4,800,204 | 1/1989 | Mueller | 514/267 |
| 4,816,258 | 3/1989 | Nedberge et al. | 424/448 |
| 4,849,226 | 7/1989 | Gale | 424/448 |
| 4,908,027 | 3/1990 | Enscore et al. | 604/890.1 |
| 4,935,429 | 6/1990 | Deckis et al. | 514/288 |
| 4,943,435 | 7/1990 | Baker et al. | 424/448 |
| 4,973,468 | 11/1990 | Chiang | 424/449 |
| 5,004,610 | 4/1991 | Osborne et al. | 424/448 |
| 5,063,234 | 11/1991 | Bryant et al. | 514/288 |
| 5,229,129 | 7/1993 | Chiang | 424/449 |
| 5,252,335 | 10/1993 | Chiang | 424/449 |
| 5,378,730 | 1/1995 | Lee et al. | 514/535 |
| 5,446,070 | 8/1995 | Mantelle | 514/772.6 |
| 5,626,866 | 5/1997 | Ebert | 424/447 |

FOREIGN PATENT DOCUMENTS

| | | |
|---|---|---|
| 4240798A1 | 6/1983 | Germany . |
| 9501167 | 1/1995 | WIPO . |

OTHER PUBLICATIONS

B.M. Knepp, et al., CRC Critical Reviews and Therapeutic Drug Carrier Systems, vol. 4, Issue 1 (1987), "Transdermal Drug Delivery: Problems and Possibilities.".

*Primary Examiner*—D. Gabrielle Brouillette
*Attorney, Agent, or Firm*—Michael J. Rafa; Steven F. Stone

[57] ABSTRACT

Composition of matter for application to a body surface or membrane to administer pergolide by permeation through the body surface or membrane, the composition comprising pergolide to be administered, at a therapeutically effective rate, alone or in combination with a permeation enhancer or mixture. Also disclosed are drug delivery devices containing the pergolide or pergolide and enhancer composition and methods for the transdermal administration of the pergolide and pergolide/enhancer composition.

30 Claims, 7 Drawing Sheets

FORMULATIONS FOR TRANSDERMAL DELIVERY OF PERGOLIDE

RELATED PATENT APPLICATIONS

This application is a Continuation-in-Part application of application Ser. No. 08/473,631, filed Jun. 7, 1995, pending, for which benefit is claimed of its filing date.

FIELD OF INVENTION

This invention relates to the safe and efficacious transdermal administration of pergolide for, among other things, the treatment of Parkinson's Disease. More particularly, the invention relates to novel methods, compositions, and devices for administering pergolide to a subject through a body surface or membrane over a sustained time period. A preferred embodiment is directed to the transdermal co-administration of a pharmaceutically acceptable salt of pergolide in combination with a permeation enhancer.

BACKGROUND OF THE INVENTION

Pergolide, 8-[(methylthio)methyl]-6-propylergoline, a compound based on the ergoline ring system, is reported to be a dopaminergic agonist that also decreases plasma prolactin concentrations. When used for treating Parkinson's Disease, pergolide is used as a conjunctive therapy with levodopa.

U.S. Pat. No. 4,166,182, incorporated herein in its entirety by reference, describes the preparation of pergolide and its oral or parenteral administration as a prolactin inhibitor and in the treatment of Parkinson's Disease.

German patent application DE 4240798, incorporated herein its entirety by reference, describes a pharmaceutical composition containing ergot derivatives, including pergolide, for protection of nerves. The composition may be delivered orally, sublingually, parenterally, percutaneously or nasally.

U.S. Pat. No. 4,797,405 incorporated herein in its entirety by reference, discusses stabilized pergolide oral compositions that demonstrate reduced decomposition when exposed to light.

The dopaminergic agonist effect of pergolide has resulted in its use in a variety of treatments, in addition to the treatment of Parkinson's Disease. For example, U.S. Pat. No. 4,800,204, incorporated herein in its entirety by reference, discusses a method of controlling tobacco use by orally or parenterally administering a direct dopamine receptor agonist such as pergolide.

U.S. Pat. No. 4,935,429, incorporated herein in its entirety by reference, discusses a method of treating psychostimulant abuse by orally or parenterally administering a dopamine agonist such as pergolide.

U.S. Pat. No. 5,063,234, incorporated herein in its entirety by reference, discusses a method of inhibiting bone demineralization by administering, preferably orally, an ergot derivative, such as pergolide.

The oral administration of pergolide in the treatment of Parkinson's Disease is initiated with 0.05 mg/day dosage for the first 2 days. The dosage is then gradually increased by 0.1 or 0.15 mg/day every third day over the next 12 days of therapy. The dosage may then be increased by 0.25 mg/day every third day until an optimum therapeutic dosage is achieved at a range of about 1.5 to 8.0 mg/day. Generally, the daily dose is divided into three oral doses. The side effects of oral administration include, but are not limited to nausea, vomiting, dizziness and orthostatic hypotension.

The transdermal route of parenteral delivery of drugs and other biologically active agents ("agents") has been proposed for a wide variety of systemically acting and locally acting agents on either a rate-controlled or non-rate-controlled basis and is described in numerous technical publications such as the following: U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,704,282; 4,788,062; 4,816,258; 4,849,226; 4,908,027; 4,943,435; and 5,004,610, the disclosures of which are incorporated in their entirety herein by reference. The transdermal administration of a related compound, lisuride, for treating Parkinson's Disease, is disclosed in U.S. Pat. Nos. 5,252,335 and 5,229,129, the disclosures of which are incorporated in their entirety herein by reference.

When first investigated in depth in the late 1960's, the transdermal route of administration appeared to offer many advantages, particularly with respect to agents that had short half lives and therefore required frequent, repeated dosing or were subject to a high degree of first-pass metabolism by the liver when orally administered. The peaks and valleys in blood concentration resulting from frequent periodic doses of short half-life agents would be eliminated and replaced by substantially constant plasma concentration. This would not only improve individual compliance but also would eliminate the alternating periods of high side-effects and ineffective blood concentrations associated with period dosing. Administering the agent through the skin directly into the blood stream would also eliminate first-pass metabolism of orally administered agents.

It was initially assumed, theoretically, that any short half-life agent of high potency and skin permeability would be suitable for safe and effective transdermal administration. This assumption, however, has not been proven true.

The failure of the transdermal route to fulfill the initial expectations of its potential as an administrative portal was primarily due to the incredible variety of properties with which nature has endowed the skin to permit it to perform its function as the primary barrier to prevent the ingress of foreign substances into the body. See Transdermal Drug Delivery: Problems and Possibilities, B. M. Knepp, et al, CRC Critical Reviews and Therapeutic Drug Carrier Systems, Vol. 4, Issue 1 (1987).

Thus, the transdermal route of administration, rather than being available to every short half-life agent of high potency and skin permeability, was found to be available only to those few agents that possess the proper combination of a host of characteristics, most of which are unpredictable, required to render the agent suitable for safe and effective transdermal administration.

The most significant of these characteristics are the following:

1. Skin Permeability. The permeability of the skin to the agent must be sufficiently high so that the agent can be administered at a therapeutically effective rate through an area of skin no greater than about 200 cm$^2$ and preferably no greater than 50 cm$^2$. The person-to-person variation in skin permeability at similar sites should also be considered.

2. Skin Binding. The skin beneath the transdermal delivery device has the capability of creating a skin depot of drug by absorbing, adsorbing, or binding a certain amount of agent. The amount of agent so bound must be supplied to the skin before the agent can be delivered into the blood stream at steady, therapeutically effective rates. If large amounts of the agent are bound in the skin, significant delays in the onset of therapeutic effect ("lag time") will be observed together with corresponding delays and termination of effect upon removal of the device. The potential also exists for toxic quantities of potent agents to be contained within the skin beneath the device. Skin binding is not related to skin permeability. Agents that are highly permeable may also be highly bound causing a lag time sufficiently long as to render them unsuitable for their intended use.

3. Irritation. The skin reacts to many topically applied substances, particularly those maintained under occlusion, by blistering or reddening accompanied by unpleasant burning, itching, and stinging sensations. Animal models are used to screen for irritation. Animal models, however, often produce both false positives and false negatives. There is also a wide interpersonal variation in susceptibility to irritation. An agent must be minimally irritating in a large percentage of the potential individual population in order to be suitable for safe and effective transdermal administration.

4. Sensitization. Sensitization is an allergic reaction which is induced when an agent is first applied to the skin and is elicited upon continued exposure which may occur immediately or after a long period of seemingly harmless exposure.

The sensitization may be local, elicited by topical exposure, which manifests itself as contact dermatitis accompanied by blistering, itching, reddening and burning at the site of application. More seriously, the sensitization may be systemic, elicited by topical application but manifesting itself by more general allergic reactions at sites other than the site of application. Most seriously, the systemic sensitization may be elicited by oral or intravenous administration of the drug. If the latter occurs, the individual will be unable to take the drug by any route of administration.

Animal models are used to screen for sensitization. Animal models, however, produce both false positives and false negatives. There is also a wide variation in the allergic reaction between individuals as well as between sexes, races and skin types. It is obvious that a useful transdermal agent must be minimally sensitizing in a large percentage of the potential individual population.

5. Pharmacokinetic Properties. The half-life of an agent is the time after administration that half of the amount administered has been eliminated from the body. Because blood concentrations of continuously administered agents will continue to increase for approximately six half-lives before steady-state constant blood concentrations are achieved, an agent must have a relatively short half-life to be suitable for continuous transdermal administration. The transdermal half-lives of most agents have not been determined. When half-lives of agents determined from intravenous administration are compared with half-lives determined from transdermal administration, the transdermal half-lives are generally longer but there can be wide variation in half-life between individuals based upon factors such as age, sex, health, and body type.

6. Pharmacodynamic Properties. Constant blood levels may not produce the desired therapeutic effects. For example, a therapeutic effect may only be observed at peak blood concentration obtained from bolus dosing but the peak concentration cannot be maintained because of side effects associated therewith. Also, continuous administration of many agents produces tolerance that may require either some agent-free interval or continually increasing and therefore potentially hazardous doses of the agent.

7. Potency. Although a certain degree of potency is required for transdermally administered agent to be effective, it is also possible for an agent to be too potent. As potency increases, lower blood concentrations are required and much smaller quantities are administered. Because of normal inter-individual variations and skin permeability, it may not be possible to precisely control whether a individual is receiving 1 $\mu$g/hr or 2 $\mu$g/hr, for example. For a highly potent agent, a 1 $\mu$g/hr administration may be totally ineffective and a 2 $\mu$g/hr rate fatal. Thus, the therapeutic index of an agent, which is the ratio of toxic blood concentration to the therapeutic blood concentration, becomes extremely significant. A highly potent agent should also have a relatively wide therapeutic window in order to be suitable for transdermal administration.

8. Metabolism. One of the perceived advantages of transdermal administration was that it avoided the "first-pass" metabolism of the agent by the liver that is associated with oral administration. It has now been recognized, however, that the skin is also a large metabolizing organ in the body for some drugs. Thus, although first-pass metabolism that occurs after an orally administered agent enters the blood stream can be avoided, skin metabolism, which occurs before the agent enters the bloodstream, cannot be avoided. Skin metabolism is capable of creating metabolites that are inert, irritating, toxic, or comparable in biological activity to that of the agent. An agent, to be suitable for transdermal administration, must have the metabolic properties that are consistent with its therapeutic use on continuous administration.

The above summarizes the primary characteristics that effect suitability of an agent for transdermal administration that have been recognized to date. There are undoubtedly others, some of which have not yet been recognized, and, in order for an agent to be suitable for transdermal administration, it must possess the right combination of all these characteristics, a combination of which, as illustrated by the very few drugs that are now suitable for administration from transdermal delivery devices, is quite rare and unpredictable.

SUMMARY OF THE INVENTION

It is unexpected that pergolide would be delivered through the skin at meaningful therapeutic rates either as a base or salt because, as its chemical name 8-[(methylthiolmethyl]-6-propylergoline monomethanesulfonate)] indicates, it has a complex chemical structure which does not lend itself to readily permeate through biological membranes such as the skin. Furthermore, it is even more unexpected that transdermal dosage forms provided with a pharmaceutically acceptable salt form of pergolide would result in a greater pergolide flux through skin than dosage forms provided with pergolide free base. Nonetheless, according to this invention, it has been discovered that pergolide can be safely and efficaciously administered transdermally to provide, among other things, treatment for Parkinson's Disease, with a reduced incidence of side effects and improved individual compliance. In addition, the present invention provides methods for the transdermal delivery of pergolide and delivery systems for effecting the same, which are suitable for the administration of pergolide continuously through a body surface or membrane to achieve and maintain therapeutic blood plasma levels of pergolide in an individual. A particularly advantageous aspect of this invention is the ability to maintain substantially constant blood plasma levels of pergolide in an individual over extended periods of time.

Surprisingly, the inventors have discovered that transdermal dosage forms provided with a pharmaceutically acceptable salt form of pergolide result in a greater pergolide flux through skin than dosage forms provided with pergolide free base. This is contrary to findings of a substantial amount of the prior art wherein for a majority of agents which have been tested for transdermal administration, it is recognized in the art that the permeability of the skin to the unionized form of the drug is generally substantially greater than that of the ionized form. A preferred embodiment is therefore directed to providing the reservoir of a transdermal delivery device with a pharmaceutically acceptable salt of pergolide, preferably pergolide mesylate, together with a permeation enhancer.

As used herein, the term "transdermal" intends percutaneous and transmucosal administration, i.e., passage of pergolide through intact unbroken skin or mucosal tissue into the systemic circulation.

As used herein, the term "pergolide" intends not only the basic form of pergolide but also pharmaceutically acceptable salt forms of pergolide.

As used herein the term "salt" intends, but is not limited to, pharmaceutically acceptable salts such as chlorides, acetates, sulfates, phosphates, and mesylates.

As used herein, the term "pergolide therapy" intends all medical conditions for which pergolide is or will be indicated, including, without limitation, as a psychic energizer and in the treatment of Parkinson's Disease, migraine, allergic responses, urticaria, hypertension, endometritis, and other conditions associated with dopaminergic agonists.

As used herein, the term "individual" intends a living mammal and includes, without limitation, humans and other primates, livestock and sports animals such as cattle, pigs and horses, and pets such as cats and dogs.

As used herein, the term "therapeutic blood plasma level" intends the level of pergolide in blood plasma that achieves a therapeutic effect and is typically within the range of about 100 pg/mL–2000 pg/mL.

As used herein, the term "therapeutically effective rate" intends a rate of pergolide delivery effective to achieve therapeutic blood plasma levels of pergolide in an individual during the administration period.

As used herein, the phrase "sustained time period" or "administration period" intends at least about 8 hours and will typically intend a period in the range of about one to about seven days.

As used herein, the phrase "predetermined area of skin" intends a defined area of intact unbroken skin or mucosal tissue. That area will usually be in the range of about 1 $cm^2$ to about 100 $cm^2$.

As used herein, the term "permeation enhance" intends an agent or a mixture of agents which increases the permeability of the skin to pergolide.

As used herein, the term "permeation enhancement" intends an increase in the permeability of skin to pergolide in the presence of a permeation enhancer as compared to permeability of skin to pergolide in the absence of a permeation enhancer.

The present invention relates to compositions, devices and methods for the transdermal administration of pergolide in the treatment of Parkinson's Disease, among other things. According to the present invention, it has been found that pergolide may be safely and efficaciously administered transdermally through a body surface or membrane at a therapeutically effective rate for a predetermined, sustained time period in order to provide an effective therapeutic result. Another aspect of the present invention is directed to the transdermal administration of pergolide together with a suitable permeation enhancer or mixture of enhancers.

The system of the invention comprises a carrier or matrix adapted to be placed in pergolide- and permeation enhancer-transmitting relation to the selected skin or other body site. The carrier or matrix contains sufficient amounts of pergolide and a permeation enhancer to continuously coadminister pergolide at a therapeutically effective rate to the site together with the permeation enhancer during the administration period.

The accompanying figures, which are incorporated in and constitute a part of this specification, illustrate embodiments of the invention and, together with the description serve to explain the principles of the invention.

DETAILED DESCRIPTION OF THE INVENTION

Figure 1:
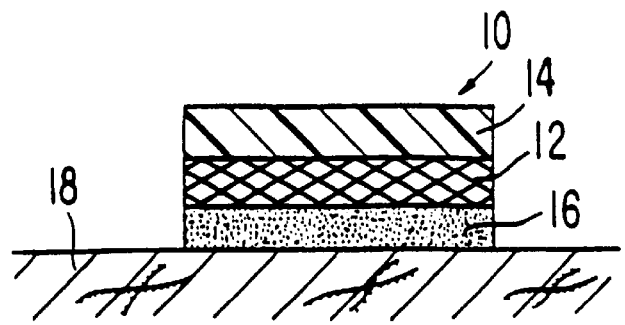
FIG. 1 is a cross-section through a schematic perspective view of one embodiment of a transdermal therapeutic system according to this invention prior to application to the skin.

According to the present invention, it has been found that pergolide may be administered to the human body at a therapeutically effective rate via the transdermal route for the purpose of treating Parkinson's Disease, among other things, when coadministered with a suitable permeation enhancer. Therapeutic blood plasma levels of 100 pg/mL to 2000 pg/mL can be achieved according to this invention. Representative in vitro skin fluxes of pergolide through human skin are in the range of 0.1–8.0 $\mu g/cm^2 \cdot hr$, depending on the form of pergolide (base or salt), the permeation enhancer, and whether an in-line contact adhesive was present in the path of drug flow. According to this invention, it is preferable to administer pergolide at a flux of at least about 1.0 $\mu g/cm^2 \cdot hr$.

It is estimated that therapeutic blood plasma levels can be achieved within approximately 5 to 10 hours following application of the first patch. When a subsequent system is applied, a lag period of no pergolide delivery is not experienced due to the presence of a skin depot of pergolide remaining from the prior system, thus pergolide is continuously administered throughout subsequent system applications in order to maintain therapeutic blood plasma levels of pergolide over a sustained time period. The system is easily adapted for shorter or longer duration treatments, but generally 72 hours is the preferred duration for a single treatment.

The desired pergolide admininstration rate may be achieved by increasing or decreasing the surface area of the transdermal delivery device without effecting the flux. For example, for a pergolide skin flux of 1.1 $\mu g/cm^2 \cdot hr$, a patch having a surface area of about 60 $cm^2$ would deliver approximately 1.6 mg of pergolide over a 24 hour period.

The pergolide administration rate may also be increased by increasing the flux of pergolide through skin by the use of permeation enhancers. A preferred embodiment of this invention relates to codelivery of a pharmaceutically acceptable salt of pergolide and a permeation enhancer comprising glycerol monolaurate and methyl laurate.

The present inventors also found that certain adhesives were preferred as the in-line contact adhesive when one was used in a therapeutic transdermal pergolide system. More particularly, it was found that systems using polyisobutylene adhesives as the in-line contact adhesive resulted in greater flux of pergolide through skin than when other adhesives, such as acrylate adhesives, were used.

Therefore, the present invention, in one embodiment, is directed to a composition of matter for administration to a body surface or membrane to deliver pergolide by permeation through the body surface or membrane at a therapeutically effective rate, wherein the composition comprises, in combination:

(a) a therapeutically effective amount of a pharmaceutically acceptable salt of pergolide; and (b) a permeation-enhancing amount of a permeation enhancer.

The drug may be present in the composition in an amount ranging from 0.1 to 20% by weight.

This invention finds particular usefulness in administering pergolide across skin. It is also useful, however, in administering pergolide across mucosa. According to our invention, pergolide and a permeation enhancer are placed in drug and permeation enhancer-transmitting relationship to an appropriate body surface, preferably in a pharmaceutically acceptable carrier thereof, and maintained in place for the desired administration period.

The pergolide and the permeation enhancer are typically dispersed within a physiologically compatible matrix or carrier, as more fully described below, which may be applied directly to the body as an ointment, gel, cream, suppository or sublingual or buccal tablet. When used in the form of a liquid, ointment, lotion, cream or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of topical compositions as are known to the art.

In other embodiments, the pergolide and the permeation enhancer would be administered from a transdermal device as more fully described below. Examples of suitable transdermal delivery devices are illustrated in FIGS. 1–4. In the figures, the same reference numbers are used throughout the different figures to designate the same or similar components. The figures are not drawn to scale.

Referring now to FIG. 1, a preferred embodiment of a transdermal therapeutic system according to this invention comprises transdermal delivery device 10 comprising a reservoir 12, preferably in the form of a matrix containing pergolide and a permeation enhancer dispersed therein. Reservoir is sandwiched between a backing 14 and an in-line contact adhesive layer 16. The device 10 adheres to the surface of the skin 18 by means of the adhesive layer 16. The adhesive layer 16 may optionally contain the permeation enhancer and/or pergolide. A strippable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 16. Although the preferred embodiments of this invention utilize an in-line adhesive as is shown in FIG. 1, other means for maintaining the system on the skin can be employed. Such means include a peripheral ring of adhesive outside the path of the drug from the system to the skin or the use of other fastening means such as buckles, belts, and elastic arm bands.

Figure 2:
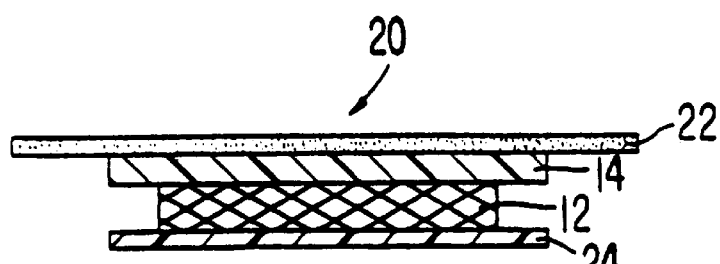
FIG. 2 is a cross-section view through another embodiment of this invention.

Alternatively, as shown in FIG. 2, transdermal therapeutic device 20 may be attached to the skin or mucosa of a individual by means of an adhesive overlay 22. Device 20 is comprised of reservoir 12, preferably in the form of a matrix containing pergolide and a permeation enhancer dispersed therein. A backing layer 14 is provided adjacent one surface of reservoir 12. Adhesive overlay 22 maintains the device on the skin and may be fabricated together with, or provided separately from, the remaining elements of the device. With certain formulations, the adhesive overlay 22 may be preferable to the in-line contact adhesive 16 as shown in FIG. 1. Backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A strippable release liner 24 is also provided with device 20 and is removed just prior to application of device 20 to the skin.

Figure 3:
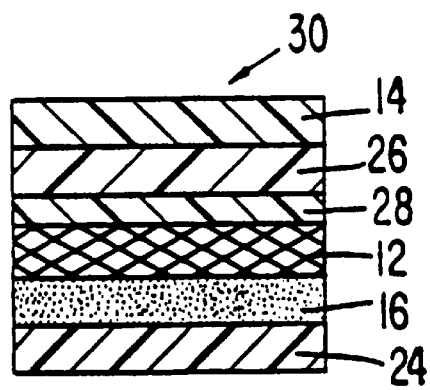
FIG. 3 is a cross-section view through another embodiment of this invention.

In FIG. 3, transdermal delivery device 30 comprises a pergolide and permeation enhancer reservoir ("pergolide reservoir") 12 substantially as described with respect to FIG. 1. Permeation enhancer reservoir ("enhancer reservoir") 26 comprises the permeation enhancer dispersed throughout and contains pergolide at or below saturation. Enhancer reservoir 26 is preferably made from substantially the same matrix as is used to form pergolide reservoir 12. A rate-controlling membrane for controlling the release rate of the permeation enhancer and/or pergolide from enhancer reservoir 26 to pergolide reservoir 12 is placed between the two reservoirs. A rate-controlling membrane (not shown in FIG. 3) for controlling the release rate of the enhancer and/or pergolide from pergolide reservoir 12 to the skin may also optionally be utilized and would be present between adhesive layer 16 and reservoir 12.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polyvinyl acetate, ethylene n-butyl acetate and ethylene vinyl acetate copolymers.

Superimposed over the permeation enhancer reservoir 26 of device 30 is a backing 14. On the skin-proximal side of reservoir 12 are an adhesive layer 16 and a strippable liner 24 which would be removed prior to application of the device 30 to the skin.

In the embodiments of FIGS. 1, 2 and 3, the carrier or matrix material of the reservoirs has sufficient viscosity to maintain its shape without oozing or flowing. If, however, the matrix or carrier is a low-viscosity flowable material such as a liquid or a gel, the composition can be fully enclosed in a pouch or pocket, as known to the art from U.S. Pat. No. 4,379,454 (noted above), for example, and as illustrated in FIG. 4. Device 40 shown in FIG. 4 comprises a backing member 14 which serves as a protective cover for the device, imparts structural support, and substantially keeps components in device 40 from escaping the device. Device 40 also includes reservoir 12, which contains the pergolide with or without a permeation enhancer, and bears on its surface distant from backing member 14, a rate-controlling membrane 28 for controlling the release of pergolide and/or permeation enhancer from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 28 are an adhesive layer 16 and a strippable liner 24 which would be removed prior to application of the device 40 to the skin.

Figure 4:
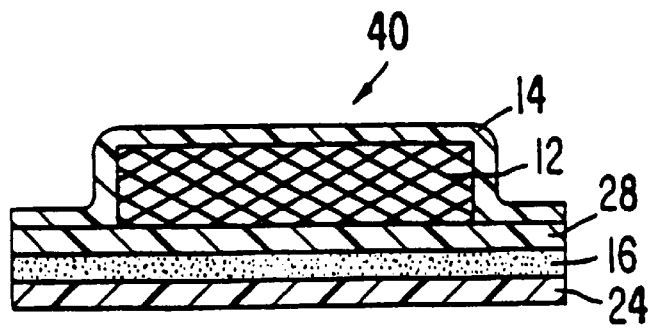
FIG. 4 is a cross-section view through another embodiment of this invention.

In an alternative embodiment of device 40 of FIG. 4, reservoir 12 contains the permeation enhancer and contains pergolide at or below saturation. The pergolide and an additional amount of permeation enhancer are present in adhesive layer 16, which acts as a separate reservoir.

The pergolide and the permeation enhancer can be administered to human skin or mucosa by direct application to the skin or mucosa in the form of an ointment, gel, cream or lotion, for example, but are preferably administered from a skin patch or other known transdermal delivery device which contains a saturated or unsaturated formulation of the pergolide and enhancer. The formulation may be aqueous or non-aqueous based. The formulation should be designed to deliver the pergolide at the necessary fluxes. Aqueous formulations typically comprise water or water/ethanol and about 1–5 wt % of a gelling agent, an example being a hydrophilic polymer such as hydroxyethylcellulose or hydroxypropylcellulose. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with the drug and the permeation-enhancing mixture, if used, in addition to any other components in the formulation.

The reservoir matrix should be compatible with pergolide, the permeation enhancer, and any carrier therefor. The term "matrix" as used herein refers to a well-mixed composite of ingredients fixed into shape. When using an aqueous-based formulation, the reservoir matrix is preferably a hydrophilic polymer, e.g., a hydrogel.

When using a non-aqueous based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would consist essentially of a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 9% to 40% VA. Polyisobutylene/oil polymers containing from 4–25% high molecular weight polyisobutylene and 20–81% low molecular weight polyisobutylene with the balance being an oil such as mineral oil or polybutene may also be used as the matrix material.

The amount of pergolide present in the therapeutic device and required to achieve an effective therapeutic result depends on many factors, such as the minimum necessary dosage of the pergolide for the particular indication being treated; the solubility and permeability of the matrix, taking into account the presence of a permeation enhancer, of the adhesive layer and of the rate-controlling membrane, if present; and the period of time for which the device will be fixed to the skin. The minimum amount of pergolide is determined by the requirement that sufficient quantities of pergolide must be present in the device to maintain the desired rate of release over the given period of application. The maximum amount for safety purposes is determined by the requirement that the quantity of pergolide present cannot exceed a rate of release that reaches toxic levels.

The pergolide is normally present in the matrix or carrier at a concentration in excess of saturation, the amount of excess being a function of the desired length of the delivery period of the system. Pergolide may, however, be present at a level below saturation without departing from this invention as long as it is continuously administered to the skin or mucosal site at a therapeutic rate and for a period of time sufficient to deliver a therapeutically effective amount of pergolide that provides the desired therapeutic result.

The permeation enhancer according to this invention comprises a monoglyceride or mixture of miniglycerides of a fatty acid and an alkyl laurate. A preferred enhancer comprises glycerol monolaurate and methyl laurate. Methyl laurate has been found to be particularly desirable as it is obtainable at a high degree of purity, thus providing a purer and better defined permeation enhancer and a system which is more readily characterized. Additionally, the inventors have found that the addition of mineral oil to the pergolide reservoir comprising glycerol monolaurate and methyl laurate provides a surprising and synergistic effect to the pergolide skin flux. In a particularly preferred embodiment, the ratio of glycerol monolaurate/methyl laurate/mineral oil is 0.75/1.0/0.50. As used herein, "mineral oil" refers to a mixture of liquid hydrocarbons of petroleum. Polybutene may also be substituted for the mineral oil.

Typically, monoglycerides have been available as a mixture of monoglycerides of fatty acids with one monoglyceride being the principal component, from which component the mixture derives its name. For example, one commercial monoglyceride is Emerest 2421 glycerol monooleate (Emery Division, Quantum Chemical Corp.), which is a mixture of glycerol oleates with a glycerol monooleate content of 58% and a total monoesters content of 58%. Other examples of commercial monoglycerides are Myverol 1899K glycerol monooleate (Eastman Chemical Products) which has a glycerol monooleate content of 61% and a total monoesters content of 93%, and Myverol 1892K glycerol monolinoleate which has a glycerol monolinoleate content of 68% and a minimum total monoesters content of 90%. The monoesters are chosen from those with from 10 to 20 carbon atoms. The fatty acids may be saturated or unsaturated and include, for example, lauric acid, myristic acid, stearic acid, oleic acid, linoleic acid and palmitic acid. Monoglyceride permeation enhancers include glycerol monooleate, glycerol monolaurate and glycerol monolinoleate, for example. In a presently preferred embodiment of this invention, the permeation enhancer comprises glycerol monolaurate as the monoglyceride.

It has been seen that glycerol monooleate having a total monoesters content of less than about 65% interacts adversely with known adhesive materials to such an extent that the adhesive cannot function to maintain a delivery device on the skin. Therefore, when an in-line adhesive is present as a part of the device of the invention so that a permeation enhancer must pass through the adhesive, and when glycerol monooleate is utilized as the permeation enhancer, the glycerol monooleate must have a total monoesters content of at least 65%.

The permeation-enhancing mixture is dispersed through the matrix or carrier, preferably at a concentration sufficient to provide permeation-enhancing amounts of enhancer in the reservoir throughout the anticipated administration period. Where there is an additional, separate permeation enhancer matrix layer as well, as in FIGS. 3 and 4, the permeation enhancer normally is present in the separate reservoir in excess of saturation.

In addition to the pergolide and permeation enhancer, the matrix or carrier may also contain dyes, pigments, inert fillers, excipients and other conventional components of pharmaceutical products or transdermal devices known to the art.

Because of the wide variation in skin permeability from individual to individual and from site to site on the same body, it may be preferable that the pergolide and permeation enhancer be administered from a rate-controlled transdermal delivery device. Rate control can be obtained either through a rate-controlling membrane or adhesive or both as well as through the other means.

A certain amount of pergolide will bind reversibly to the skin, and it is accordingly preferred that the skin-contacting layer of the device include this amount of pergolide as a loading dose.

The surface area of the device of this invention can vary from about 1–200 cm$^2$. A typical device, however, will have a surface area within the range of about 1–50 cm$^2$, preferably about 20 cm$^2$.

The devices of this invention can be designed to effectively deliver pergolide for an extended time period of from several hours up to 7 days or longer. Seven days is generally the maximum time limit for application of a single device because the adverse effect of occlusion of a skin site increases with time and the normal cycle of sloughing and replacement of the skin cells occurs in about 7 days.

Preferably, the transdermal drug delivery device contains sufficient amounts of a permeation enhancer as described above and pergolide, in combination, to provide systemic administration of pergolide through the skin at a therapeutically effective rate during the administration period in order to provide therapeutic blood plasma levels.

Preferably, a device for the transdermal administration of pergolide, at a therapeutically effective rate, comprises:

(a) a reservoir comprising:
  (i) 1–15% by weight of a pharmaceutically acceptable salt of pergolide,
  (ii) 10–70% by weight of a permeation enhancer,
  (iii) 35 to 85% by weight ethylene vinyl acetate having a vinyl acetate content of 9–60%;
(b) a backing behind the skin-distal surface of the reservoir; and
(c) means for maintaining the reservoir in drug- and permeation enhancer-transmitting relation with the skin.

More preferably, a device for the transdermal administration of pergolide, at a therapeutically effective rate, comprises:

(a) a reservoir comprising:
  (i) 1 to 15% by weight of a pharmaceutically acceptable salt of pergolide,
  (ii) 10 to 70% by weight of a permeation enhancer,
  (iii) 45 to 85% by weight ethylene vinyl acetate having a vinyl acetate content of 9–40%;
(b) a backing behind the skin-distal surface of the reservoir; and
(c) means for maintaining the reservoir in drug- and permeation enhancer-transmitting relation with the skin.

Most preferably, a device for the transdermal administration of pergolide, at a therapeutically effective rate, comprises:

(a) a reservoir comprising:
  (i) 1 to 15% by weight pergolide mesylate,
  (ii) 1–35% by weight glycerol monolaurate,
  (iii) 1–35% by weight methyl laurate,
  (iv) 1–35% by weight mineral oil,
  (v) 45 to 80% by weight ethylene vinyl acetate having a vinyl acetate content of 30–40%;
(b) a backing behind the skin-distal surface of the reservoir; and
(c) means for maintaining the reservoir in drug- and permeation enhancer-transmitting relation with the skin.

The backing may be a breathable or occlusive material such as polyethylene, polyurethane, polyester or ethylene vinyl acetate films. If mineral oil is used, a polyester backing is preferred. If an ethylene vinyl acetate is employed as the backing, preferably, it has an acetate content of 33% or 40%.

The means for maintaining the reservoir in drug and permeation enhancer transmitting relation with the skin are preferably a polyisobutylene adhesive, as described in the Examples that follow. A further embodiment of the invention is directed to including in the adhesive a small percentage, e.g., from about 1.0 to about 5 wt % of pergolide.

The aforementioned patents describe a wide variety of materials which can be used for fabricating various layers or components of the transdermal pergolide delivery systems according to this invention. This invention, therefore, contemplates the use of other materials other than those specifically disclosed herein including those which may become hereafter known to the artist capable of forming the necessary functions.

The invention is also directed to a method of continuously administering pergolide to a individual at a therapeutically effective rate during an administration period in order to provide substantially constant therapeutic blood plasma levels of pergolide in an individual.

Another method of the present invention is directed to a method for the transdermal coadministration of pergolide at a therapeutically effective rate together with a skin permeation-enhancing amount of a permeation enhancer in order to achieve and maintain therapeutic blood plasma levels of pergolide in an individual, comprising:

(a) coadministering to a body surface or membrane, pergolide; and (b) a permeation enhancer, wherein pergolide is delivered at a therapeutically effective rate during the administration period in order to achieve and maintain therapeutic blood plasma levels of pergolide in an individual. The pergolide and permeation enhancer may be administered to the body surface or membrane by means of the devices and compositions described above.

A preferred embodiment of the present invention comprises a method of treating Parkinson's Disease. To be useful in treating Parkinson's Disease, pergolide should be present above plasma concentrations of about 100 pg/mL, preferably at concentrations above about 300 pg/mL and most preferably at concentrations of about 1000 pg/mL. To achieve this result, pergolide is delivered at an estimated therapeutic rate of at least about 100 µg per hour, but typically of at least 125 µg/hr, and more typically at about 150 µg/hr, for the treatment period, usually about 12 hours to 7 days. For example, a 20 cm² system would require a pergolide flux through skin of 7.5 µg/cm²·hr in order to achieve the desired therapeutic rate of 150 µg/hr. Alternatively, three 25 cm² systems would require a pergolide flux of about 2 µg/cm²·hr to achieve the administration rate of 150 µg/hr. Such regimens would deliver approximately 3.6 mg of pergolide over a 24 hour period.

The length of time of pergolide presence and the total amount of pergolide in the plasma can be changed following the teachings of this invention to provide different treatment regimens. Thus, they can be controlled by the amount of time during which exogenous pergolide is delivered transdermally to an individual or animal.

Having thus generally described our invention, the following specific examples describe preferred embodiments thereof but are not intended to limit the invention in any manner.

EXAMPLE 1

Figure 5:
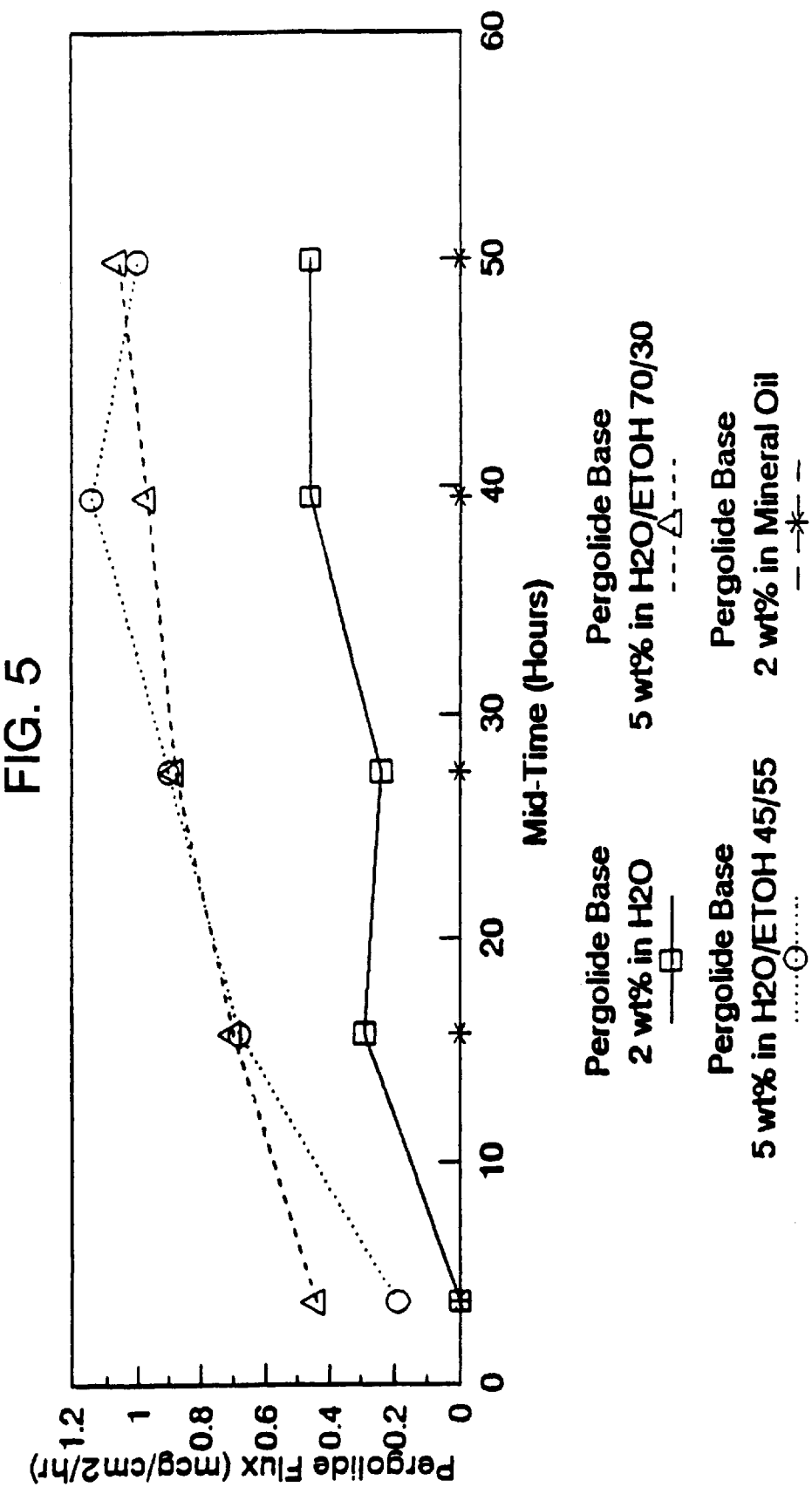
FIG. 5 is a graph of the flux of pergolide base through human epidermis, in vitro, at 35° C., from various aqueous and non-aqueous donors.
Figure 6:
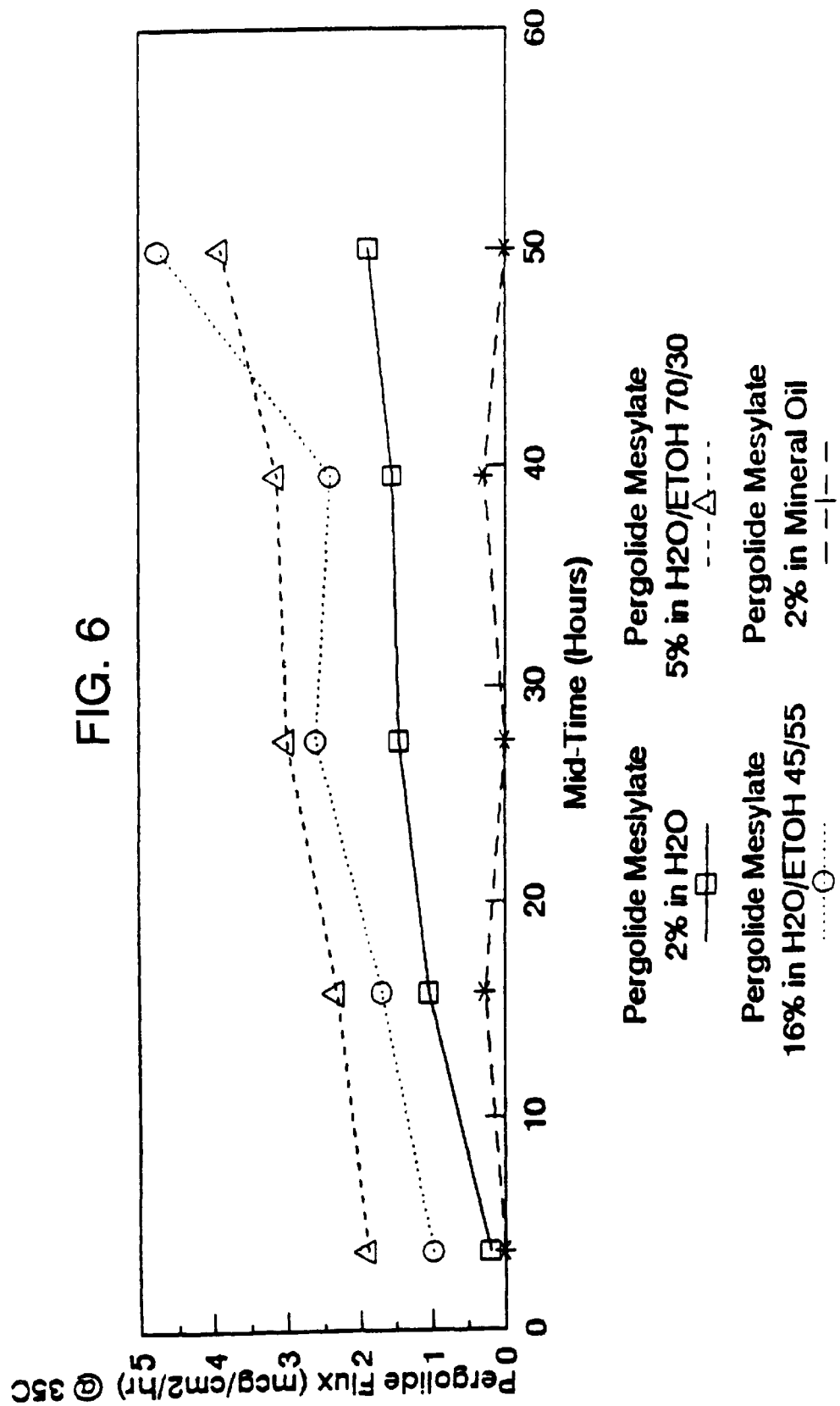
FIG. 6 is a graph of the flux of pergolide mesylate through human epidermis, in vitro, at 35° C., from various aqueous and non-aqueous donors.

Several test samples were made to measure the flux of pergolide base and mesylate through human cadaver epidermis from donor vehicles containing the pergolide base or mesylate mixed with water alone, water and ethanol, or mineral oil alone as shown in Table 1. Transdermal fluxes were obtained using human epidermis at 35° C. in standard diffusion cells. FIGS. 5 and 6 graphically depict the results. As seen in these Figures, the average baseline skin flux of pergolide base without any permeation enhancer is approximately 0.3 µg/cm²·hr over a fifty two hour period, while the average baseline skin flux of pergolide mesylate without permeation enhancers is approximately 1.1 µg/cm²·hr over the same time period.

TABLE 1

Aqueous and Non-Aqueous Donor Solutions (weight percent)

| Pergolide (form and content) | H₂O | EtOH | Mineral Oil |
|---|---|---|---|
| Base 2 | 98 | 0 | 0 |
| Base 5 | 45 | 55 | 0 |

TABLE 1-continued

Aqueous and Non-Aqueous Donor Solutions (weight percent)

| Pergolide (form and content) | H₂O | EtOH | Mineral Oil |
|---|---|---|---|
| Base 5 | 70 | 30 | 0 |
| Base 2 | 0 | 0 | 98 |
| Mesylate 2 | 98 | 0 | 0 |
| Mesylate 5 | 45 | 55 | 0 |
| Mesylate 5 | 70 | 30 | 0 |
| Mesylate 2 | 0 | 0 | 98 |

EXAMPLE 2

The drug/permeation enhancer reservoirs were prepared by mixing ethylene vinyl acetate having a vinyl acetate content of 40 percent ("EVA 40", USI Chemicals, Illinois), pergolide mesylate, GML, and a cosolvent selected from Laureth-4 (L4) (Heterene Chemical Co., Inc., Paterson, N.J.), methyl laurate (Sigma), lauryl lactate (ISP Van Dyk Inc., Belleville, N.J.) and dodecyl acetate (Penta). The mixture was then dissolved in tetrahydrofuran. After blending, the mixture was hand cast and dried to a 5 mil. thick film. Various compositions for each cosolvent without mineral oil were compared with a control composition comprising mesylate/GML/laureth-4/EVA 10/20/12158. The compositions of the drug reservoirs is shown in Tables 4a–4c.

TABLE 4a

Drug/Permeation Enhancer Reservoir Composition (weight percent)

| Pergolide mesylate | GML | Methyl Laurate | EVA 40 |
|---|---|---|---|
| 5 | 17 | 3 | 75 |
| 5 | 15 | 5 | 75 |
| 5 | 10 | 10 | 75 |

TABLE 4b

Drug/Permeation Enhancer Reservoir Composition (weight percent)

| Pergolide mesylate | GML | Dodecyl Acetate | EVA 40 |
|---|---|---|---|
| 5 | 17 | 3 | 75 |
| 5 | 15 | 5 | 75 |
| 5 | 10 | 10 | 75 |

TABLE 4c

Drug/Permeation Enhancer Reservoir Composition (weight percent)

| Pergolide mesylate | GML | Lauryl Lactate | EVA 40 |
|---|---|---|---|
| 5 | 17 | 3 | 75 |
| 5 | 15 | 5 | 75 |
| 5 | 10 | 10 | 75 |

The film was then laminated to a Medpar backing on one side. The film was then laminated to a pigmented medium density polyethylene/aluminum foil/PET/EVA (Medpar®) backing on one side. The film was then cut into circles using a stainless steel punch with an area of 1.6 cm².

Circular pieces of human epidermis were placed with stratum corneum facing up. The release liner of the laminate was removed and the system was centered over the stratum corneum side of the epidermis. The edges of epidermis were then folded around the system. This assembly was then mounted on a Teflon rod. A known volume of receptor solution was then placed in a test tube and was equilibrated at 35° C. The Teflon rod with system and epidermis attached was then placed in a water bath at 35° C. Mixing was accomplished by attachment to a motor which caused constant vertical mixing.

Figure 7:
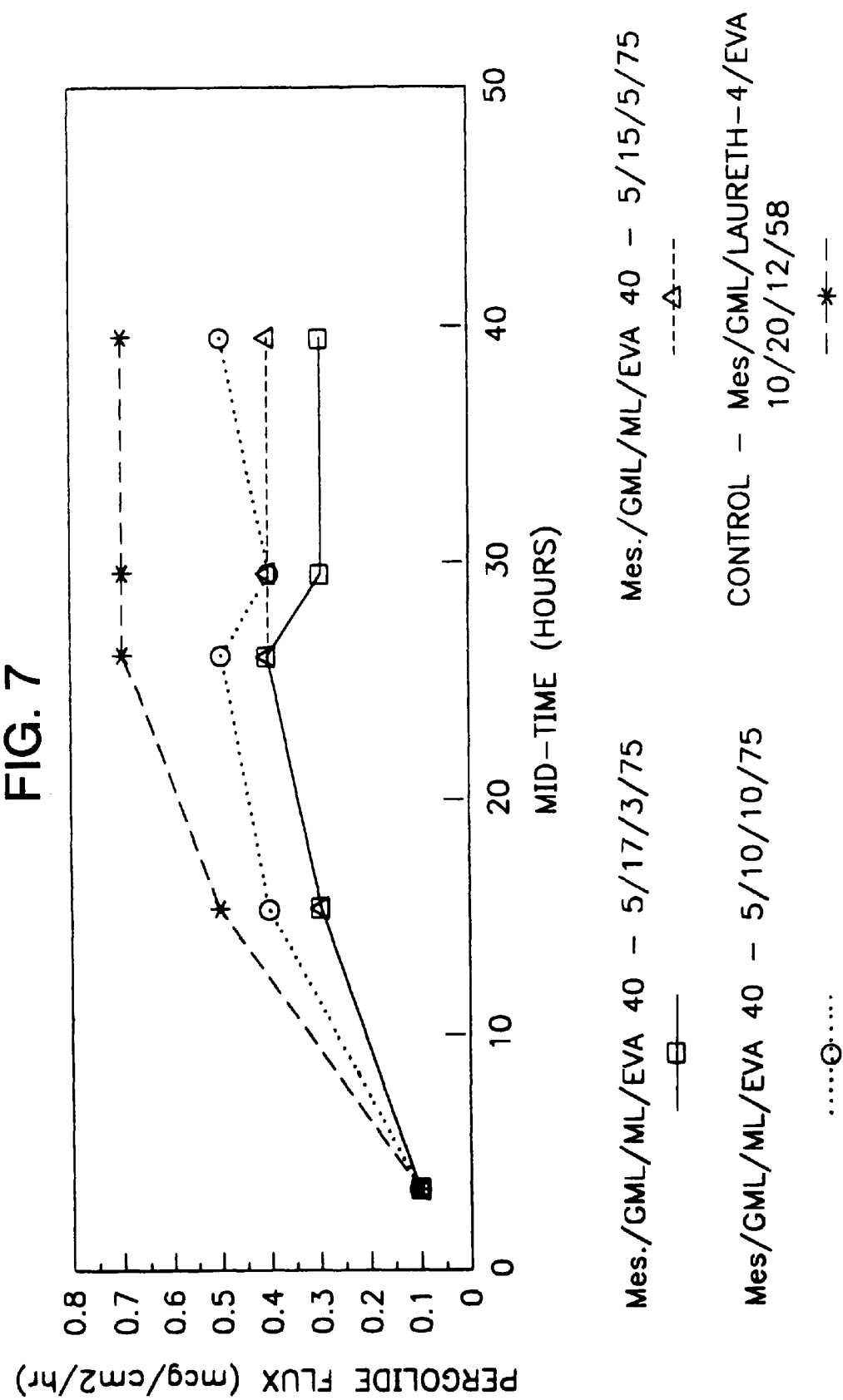
FIG. 7 is a graph of the flux of pergolide mesylate through human epidermis, in vitro, at 35° C., from various pergolide mesylate/GML/methyl laurate/EVA 40 systems with no adhesive.
Figure 8:
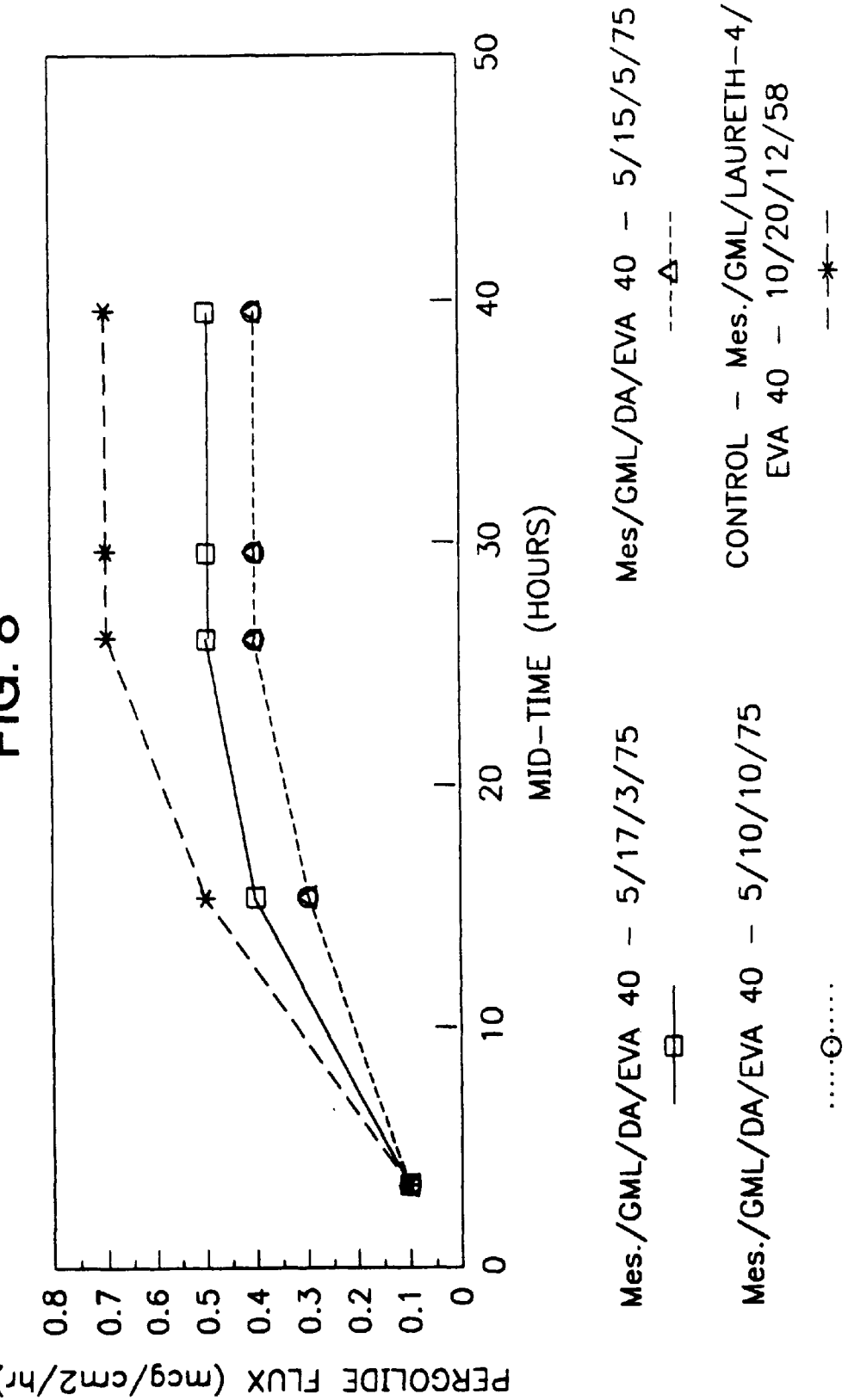
FIG. 8 is a graph of the flux of pergolide mesylate through human epidermis, in vitro, at 35° C., from various pergolide mesylate/GML/dodecyl acetate/EVA 40 systems with no adhesive.
Figure 9:
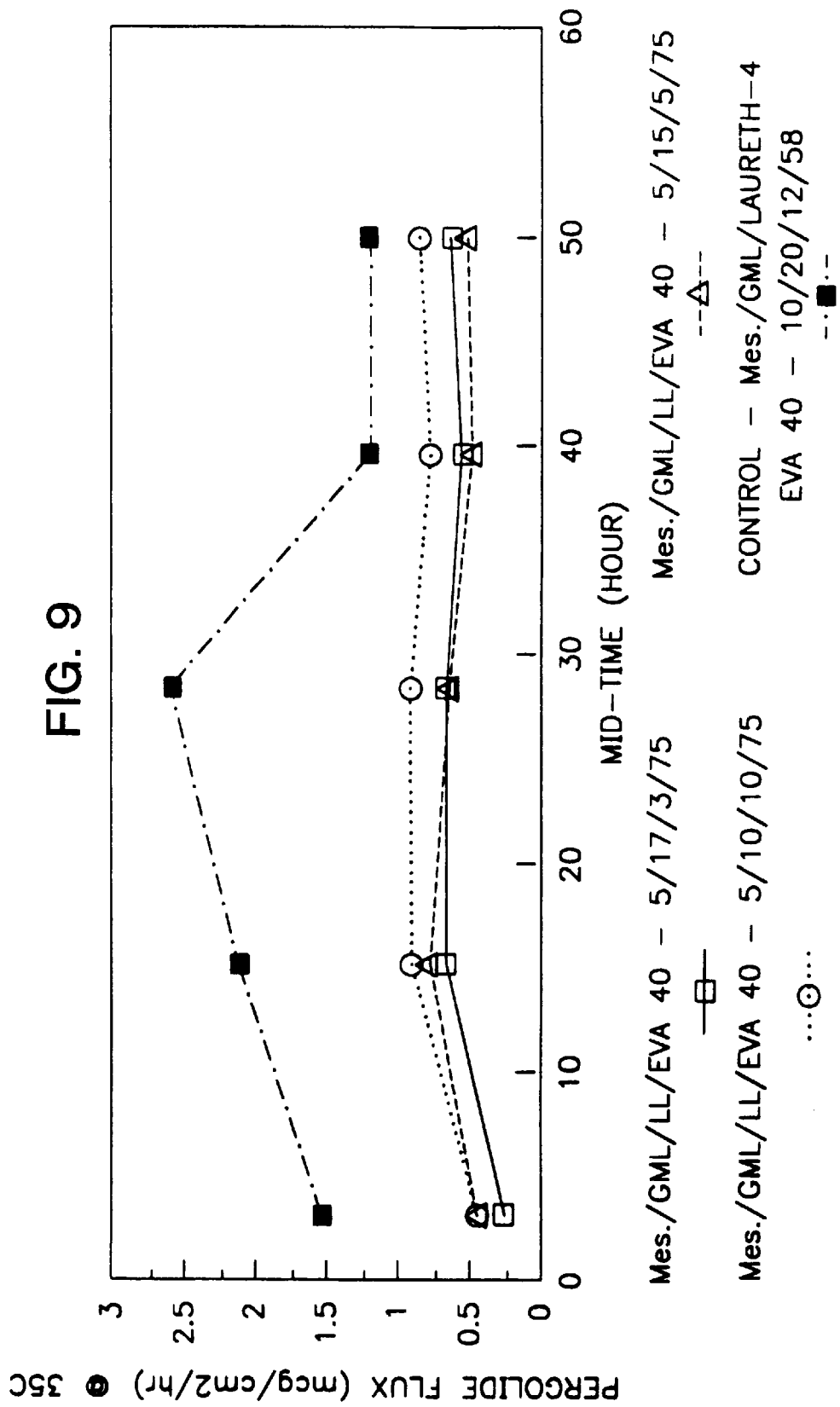
FIG. 9 is a graph of the flux of pergolide mesylate through human epidermis, in vitro, at 35° C., from various pergolide mesylate/GML/lauryl lactate/EVA 40 systems with no adhesive.

At given time intervals, the entire receptor solution was removed from the test tubes and replaced with an equal volume of fresh receptor solutions previously equilibrated at 35° C. The receptor solutions are stored in capped vials at room temperature until assayed for pergolide content by HPLC. From the drug concentration and the volume of the receptor solutions, the area of permeation and the time interval, the flux of the drug through the epidermis was calculated as follows: (drug concentration×volume of receptor)/(area×time)=flux ($\mu g/cm^2 \cdot hr$). The skin flux of pergolide mesylate is shown in FIGS. 7–9.

Figure 10:
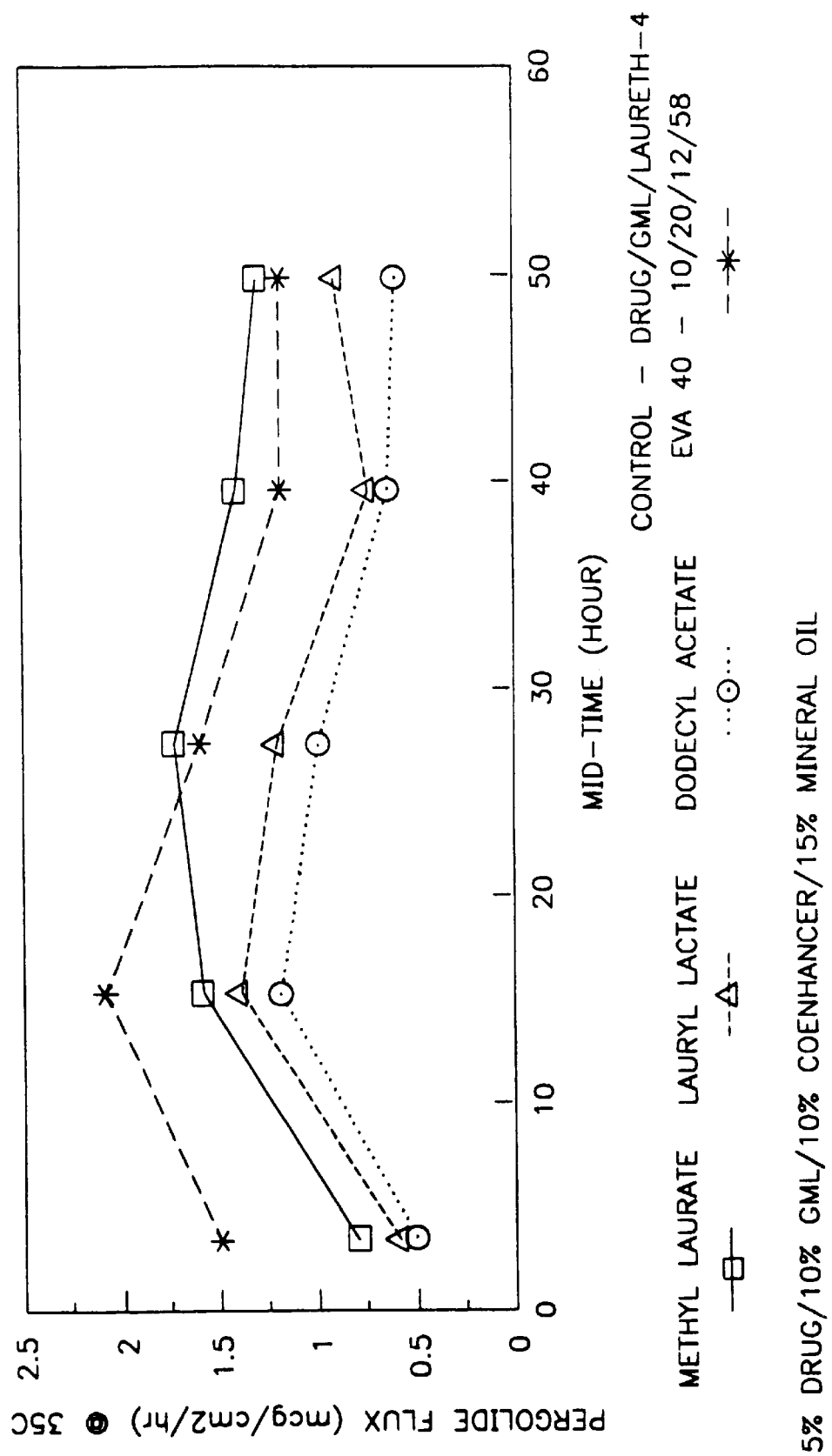
FIG. 10 is a graph of the flux comparison of GML coenhancers methyl laurate, lauryl lactate, and dodecyl acetate in combination with mineral oil through human epidermis, in vitro, at 35° C., from various pergolide mesylate/GML/coenhancer/mineral oil/EVA 40 systems with no adhesive.

Compositions comprising 5% pergolide mesylate, 10% GML, 10% of one of the lauryl lactate, methyl laurate, or dodecyl acetate cosolvents, 15% mineral oil, and 60% EVA 40 were then prepared and used in the in vitro skin flux experiment described above and compared to the pergolide mesylate/GML/laureth 4/EVA 40 10/20/12/58 control. The result of the in vitro skin flux experiment is shown in FIG. 10. As seen in FIG. 10, the mineral oil had the most substantial effect on the composition comprising GML and methyl laurate.

Having thus generally described our invention and described certain specific embodiments thereof, including the embodiments that applicants consider the best mode of practicing their invention, it should be readily apparent that various modifications to the invention may be made by workers skilled in the art without departing from the scope of this invention which is limited only by the following claims.

What is claimed is:

1. A composition of matter for delivering pergolide through the skin or mucosa by permeation through the skin or mucosa, the composition comprising an amount of a pharmaceutically acceptable salt of pergolide and a permeation-enhancing amount of a permeation enhancer comprising a monoglyceride or mixture of monoglycerides of a fatty acid and an alkyl laurate in a carrier effective to permit sustained release of pergolide over an administration period in order to deliver about 1.5–8 mg/day of pergolide at a flux greater than about 1 $\mu g/cm^2 \cdot hr$ and achieve therapeutically effective blood plasma levels of pergolide in a patient over a substantial portion of said administration period.

2. A composition according to claim 1 wherein the pharmaceutically acceptable salt is pergolide mesylate.

3. A composition according to claim 2 wherein the monoglyceride comprises glycerol monolaurate.

4. A composition according to claim 3 wherein the alkyl laurate comprises methyl laurate.

5. A composition according to claim 4 wherein the permeation enhancer further comprises mineral oil.

6. A composition according to claim 1 wherein the permeation enhancer comprises glycerol monolaurate and methyl laurate.

7. A device for the transdermal administration of pergolide at a therapeutically effective rate, comprising:

(a) a reservoir comprising an amount of a pharmaceutically acceptable salt of pergolide and a permeation-enhancing amount of a monoglyceride or mixture of monoglycerides of a fatty acid and an alkyl laurate;

(b) a backing behind the body contacting-distal surface of the reservoir; and (c) means for maintaining the reservoir in drug and permeation enhancer transmitting relation with a body surface or membrane wherein the pergolide and the permeation enhancer are provided in an amount effective to permit sustained release of pergolide over an administration period in order to deliver about 1.5–8 mg/day of pergolide at a flux greater than about 1 $\mu g/cm^2 \cdot hr$ and achieve therapeutically effective blood plasma levels of pergolide in a patient over a substantial portion of said administration period.

8. A device according to claim 7 wherein the pharmaceutically acceptable salt is pergolide mesylate.

9. A device according to claim 8 wherein the monoglyceride comprises glycerol monolaurate.

10. A device according to claim 9 wherein the alkyl laurate comprises methyl laurate.

11. A device according to claim 10 wherein the permeation enhancer further comprises mineral oil.

12. A device according to claim 7 wherein the permeation enhancer comprises glycerol monolaurate and methyl laurate.

13. A device according to claim 11 wherein the means for maintaining the reservoir in relation with the skin comprises an in-line adhesive layer on the body contacting-proximal surface of the reservoir.

14. A device according to claim 13 wherein the in-line adhesive is a polyisobutylene adhesive.

15. A device for the transdermal administration of pergolide at a therapeutically effective rate, comprising:

(a) a first reservoir comprising an amount of a pharmaceutically acceptable salt of pergolide and a permeation-enhancing amount of a monoglyceride or mixture of monoglycerides of a fatty acid and an alkyl laurate;

(b) a second reservoir comprising an excess of the permeation enhancer and the pharmaceutically acceptable salt of pergolide at or below saturation;

(c) a rate-controlling membrane between the first reservoir and the second reservoir;

(d) a backing behind the body contacting-distal surface of the second reservoir; and (e) means for maintaining the first and second reservoirs in drug-and permeation enhancer-transmitting relation with a body surface or membrane wherein the pergolide and the permeation enhancer are provided in an amount effective to permit sustained release of pergolide over an administration period in order to deliver about 1.5–8 mg/day of pergolide at a flux greater than about 1 $\mu g/cm^2 \cdot hr$ and achieve therapeutically effective blood plasma levels of pergolide in a patient over a substantial portion of said administration period.

16. A device according to claim 15 wherein the pharmaceutically acceptable salt is pergolide mesylate.

17. A device according to claim 16 wherein the monoglyceride comprises glycerol monolaurate.

18. A device according to claim 17 wherein the alkyl laurate comprises methyl laurate.

19. A device according to claim 18 wherein the permeation enhancer further comprises mineral oil.

20. A device according to claim 15 wherein the permeation enhancer comprises glycerol monolaurate and methyl laurate.

21. A device according to claim 19 wherein the means for maintaining the reservoir in relation with the skin comprises an in-line adhesive layer on the body contacting-proximal surface of the reservoir.

22. A device according to claim 21 wherein the in-line adhesive is a polyisobutylene adhesive.

23. A device for the transdermal administration of pergolide at a therapeutically effective rate, comprising:
   (a) a reservoir comprising:
      (i) 1 to 20 wt % of a pharmaceutically acceptable salt of pergolide;
      (ii) 5 to 60 wt % of permeation enhancer comprising glycerol monolaurate and methyl laurate;
      (iii) 30 to 90 wt % of ethylene vinyl acetate copolymer;
   (b) a backing behind the body contacting-distal surface of the reservoir; and
   (c) means for maintaining the reservoir in drug-and permeation enhancer-transmitting relation with a body surface or membrane, wherein pergolide is delivered over an administration in order to deliver about 1.5–8 mg/day of pergolide at a flux greater than about 1 $\mu g/cm^2 \cdot hr$ and achieve therapeutically effective blood plasma levels of pergolide in a patient over a substantial portion of said administration period.

24. A device according to claim 23 wherein the pharmaceutically acceptable salt is pergolide mesylate.

25. A device according to claim 24 wherein the permeation enhancer comprises 5–20 wt % glycerol monolaurate and 5–20 wt % methyl laurate.

26. A device according to claim 25 wherein the permeation enhancer additionally comprises 5–25 wt % mineral oil.

27. A method for the transdermal administration of pergolide by permeation through a body surface or membrane at a therapeutically effective rate, which method comprises co-administering a pharmaceutically acceptable salt of pergolide and a permeation enhancer comprising glycerol monolaurate and methyl laurate to a body surface or membrane in a carrier effective to permit sustained release of pergolide in order to deliver about 1.5–8 mg/day of pergolide at a flux in excess of about 1 $\mu g/cm^2 \cdot hr$ and achieve therapeutically effective blood plasma levels of pergolide in a patient over a substantial portion of said administration period.

28. A method according to claim 27 wherein the pharmaceutically acceptable salt is pergolide mesylate.

29. A method according to claim 28 wherein the permeation enhancer additionally comprises mineral oil.

30. A method according to claim 28 wherein said blood plasma levels are maintained in the range of about 300–1200 pg/mL.

* * * * *